United States Patent [19]
Kokemüller et al.

[11] Patent Number: 6,025,199
[45] Date of Patent: Feb. 15, 2000

[54] METHOD FOR MONITORING CORROSION

[75] Inventors: Detlef Kokemüller, Herzogenaurach; Margit Adloff, Schwarzenbruck; Konrad Bitter, Herzogenaurach, all of Germany

[73] Assignee: Siemens Aktiengesellschaft, Munich, Germany

[21] Appl. No.: 09/243,297

[22] Filed: Feb. 2, 1999

Related U.S. Application Data

[63] Continuation of application No. PCT/EP97/03931, Jul. 21, 1997.

[51] Int. Cl.⁷ .................................................... G01N 31/00
[52] U.S. Cl. .............................. 436/6; 436/55; 436/144; 134/18; 134/41
[58] Field of Search ................. 436/6, 144, 55; 422/53; 73/23.35, 23.41; 134/3, 18, 41

[56] References Cited

U.S. PATENT DOCUMENTS

| | | | |
|---|---|---|---|
| 4,056,968 | 11/1977 | Winslow, Jr. et al. | 73/19 |
| 4,124,408 | 11/1978 | Eaton et al. | |
| 4,137,047 | 1/1979 | Kim | |
| 5,392,661 | 2/1995 | Freeman | 73/866 |

FOREIGN PATENT DOCUMENTS

| | | |
|---|---|---|
| 0531149A2 | 3/1993 | European Pat. Off. |
| 266 288 A1 | 3/1989 | Germany |

OTHER PUBLICATIONS

Japanese Patent Abstract No. 01176081 (Yoshiyuki et al.), dated Jul. 12, 1989.

"Dissolved Hydrogen Analyzer—A Tool for Boiler Corrosion Studies", Clarence Jacklin et al., Materials protection and Performance, May 1971, pp. 39–44.

*Primary Examiner*—Robert J. Warden, Sr.
*Assistant Examiner*—Kaj K. Olsen
*Attorney, Agent, or Firm*—Herbert L. Lerner; Laurence A. Greenberg

[57] ABSTRACT

A method for monitoring the corrosion of C-steel of a vessel, in particular of a steam generator, when the vessel is being cleaned using at least one chemical which releases a gas, in particular nitrogen, during the cleaning process. It is envisaged that the volumetric ratio or quantitative ratio between hydrogen and the gas released is determined in the gas/vapor mixture which forms during the cleaning process and this ratio is compared with a threshold value. The cleaning process is interrupted in the event the threshold value is exceeded.

10 Claims, No Drawings

METHOD FOR MONITORING CORROSION

CROSS-REFERENCE TO RELATED APPLICATION

This is a continuation of copending International Application PCT/EP97/03931, filed Jul. 21, 1997, which designated the United States.

BACKGROUND OF THE INVENTION

Field of the Invention

The invention relates to a method for monitoring the corrosion of C-steel of a vessel, in particular of a steam generator, while the vessel is being cleaned using at least one chemical which releases a gas, in particular nitrogen, during the cleaning process.

When cleaning vessels, which are, for example, steam generators in a nuclear power plant, the intention is to dissolve deposits with chemicals. The deposits often include magnetite. After the deposits have been removed, suitable chemicals attack the material of the vessel. At individual locations, the chemicals often penetrate through to the material of the vessel and attack the material even before the vessel has been sufficiently cleaned. When this happens, hydrogen is released.

Various methods for detecting that the chemicals are attacking the steel of the vessel have already been proposed, including measuring the hydrogen produced by corrosion, or electrochemical measurements.

However, the known methods cannot be used to establish the extent of progress of the overall cleaning operation. If the chemical reaches the C-steel on only a relatively small part of the vessel inner wall, hydrogen is released even though most of the vessel has not yet been cleaned and is still covered, for example with magnetite.

SUMMARY OF THE INVENTION

It is accordingly an object of the invention to provide a method for monitoring corrosion which overcomes the abovementioned disadvantages of the prior art methods of this general type.

The invention is based on the object for providing a method for monitoring corrosion that can be used to establish not only whether the material of the vessel is being attacked but also whether the cleaning operation is sufficiently far advanced.

The object is achieved according to the invention by the fact that the volumetric ratio or quantitative ratio between hydrogen and a gas released is determined to be present in a gas/vapor mixture which forms during the cleaning process. The ratio is compared with a threshold value, and the cleaning process is interrupted in the event that the threshold value is exceeded.

Other features which are considered as characteristic for the invention are set forth in the appended claims.

Although the invention is described herein as embodied in a method for monitoring corrosion, it is nevertheless not intended to be limited to the details described, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments.

DESCRIPTION OF THE PREFERRED EMBODIMENT

A volume or quantity of gas released during a cleaning process of C-steel of a vessel, in particular of a steam generator, while the vessel is being cleaned using at least one chemical which releases the gas, in particular nitrogen gas, provides an indication of the current intensity of the cleaning process. During the cleaning process a volume or quantity of hydrogen gas is also released and provides an indication of the current intensity with which the metal of the vessel is being attacked. Therefore, the ratio between the two volumes or quantities makes it possible to state whether or not the benefit provided by the cleaning process outweighs the problems presented by the attack on the metal. A threshold value for the ratio between the volumes or quantities of hydrogen and the gas released, which may, for example, be nitrogen, may be selected in such a way that, in the event of the threshold value being exceeded, the drawbacks outweigh the benefit of the cleaning process. Consequently, the cleaning process is interrupted in the event of the threshold value being exceeded.

The method according to the invention provides the benefit that the cleaning process can be continued until an optimum time despite a slight incipient attack on the metal.

The chemical used in the cleaning is, for example, a complexing agent that includes, for example, $NH_3$—EDTA and hydrazine.

In order for hydrogen and the released gas (e.g. nitrogen) to be measured, the gas/vapor mixture from the vessel is fed, for example via a pipeline, to one or more measuring units. The measuring units may be a unit for measuring hydrogen and a unit for measuring the gas released, e.g. nitrogen. As a result, it is possible for the volumes or quantities released to be measured continuously, so that the ratio between hydrogen and the released gas can also be determined continuously and can be continuously compared with the threshold value.

By way of example, the levels of hydrogen and of the released gas (e.g. nitrogen) in the gas/vapor mixture are measured using a gas chromatograph. This results in a high level of measuring accuracy.

The threshold value for the volumetric ratio or quantitative ratio between hydrogen and the released gas (e.g. nitrogen), above which the cleaning is interrupted, is, for example, between 1 and 2. A particularly suitable threshold value is 1.4.

The method according to the invention provides the advantage, in particular, that monitoring the ratio between hydrogen and the gas released during the cleaning process makes it possible to have some indication of whether or not the problems presented by the chemicals attacking the C-steel of the vessel outweigh the benefit provided by further cleaning (dissolution of magnetite) in the vessel.

Furthermore, calibration of the method even allows the metal attack rates in mm/h to be monitored.

We claim:

1. A method for monitoring corrosion of C-steel of a vessel in a cleaning process of the vessel using at least one chemical which releases a gas during the cleaning process, which comprises:

determining one of a volumetric ratio and a quantitative ratio between hydrogen gas and the gas released in a gas/vapor mixture formed during the cleaning process;

comparing one of the volumetric ratio and the quantitative ratio with a threshold value; and interrupting the cleaning process if the threshold value is exceeded.

2. The method according to claim 1, which comprises using a complexing agent as the at least one chemical used in the cleaning process.

3. The method according to claim 2, which comprises using $NH_3$—EDTA and hydrazine as the complexing agent.

4. The method according to claim 1, which comprises feeding the gas/vapor mixture, via a pipeline, to one or more units for measuring the hydrogen and the gas released.

5. The method according to claim 1, which comprises measuring levels of the hydrogen and of the gas released in the gas/vapor mixture using a gas chromatograph.

6. The method according to claim 1, wherein the threshold value lies between 1 and 2.

7. The method according to claim 6, wherein the threshold value is 1.4.

8. The method according to claim 1, which comprises monitoring a metal attack rate in mm/h by a calibration process.

9. The method according to claim 1, which comprises monitoring a steam generator as the vessel being cleaned.

10. The method according to claim 1, which comprises measuring nitrogen gas as the gas released from the gas/vapor mixture.

* * * * *

UNITED STATES PATENT AND TRADEMARK OFFICE
CERTIFICATE OF CORRECTION

PATENT NO. : 6,025,199
DATED : February 15, 2000
INVENTOR(S) : Detlef Kokemüller, Margit Adloff, Konrad Bitter It is certified that error appears in the above-identified patent and that said Letters Patent is hereby corrected as shown below:

Title page,
Item [30] should read as follows:

Aug. 2, 1996 [DE] Germany.......... 196 31 178.0

Signed and Sealed this

Twenty-eighth Day of November, 2000

Attest:

Q. TODD DICKINSON

*Attesting Officer*        *Director of Patents and Trademarks*